United States Patent
Lee et al.

(10) Patent No.: US 7,638,333 B2
(45) Date of Patent: *Dec. 29, 2009

(54) ANTHRAX VACCINE

(75) Inventors: John S. Lee, Hagerstown, MD (US);
Peter Pushko, Frederick, MD (US);
Michael D. Parker, Frederick, MD
(US); Jonathan F. Smith, Sabillasville,
MD (US); Susan L. Welkos, Frederick,
MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1009 days.

This patent is subject to a terminal disclaimer.

(21) Appl. No.: 10/442,502

(22) Filed: May 21, 2003

(65) Prior Publication Data

US 2004/0009945 A1 Jan. 15, 2004

(51) Int. Cl.
*C12N 15/86* (2006.01)
*A01N 43/04* (2006.01)

(52) U.S. Cl. ............. 435/456; 435/455; 435/320.1; 435/325; 514/44; 424/93.1; 536/23.7; 536/23.4

(58) Field of Classification Search ............... None
See application file for complete search history.

(56) References Cited

U.S. PATENT DOCUMENTS 5,591,631 A * 1/1997 Leppla et al. ............ 435/252.3
5,677,274 A * 10/1997 Leppla et al. ................ 514/2
6,592,872 B1 * 7/2003 Klimpel et al. ......... 424/197.11
6,770,479 B1 * 8/2004 Lee et al. ................ 435/456
2002/0034512 A1 * 3/2002 Ivins et al. .............. 424/184.1
2002/0137058 A1 * 9/2002 Mirkin et al. .................. 435/6

FOREIGN PATENT DOCUMENTS

| WO | 94/18332 | * | 8/1994 |
| WO | WO 95/07994 | | 3/1995 |
| WO | WO 96/17067 | | 6/1996 |
| WO | WO 96/37616 | | 11/1996 |
| WO | WO 98/08952 | | 3/1998 |

OTHER PUBLICATIONS

Singh, Y et al, The Journal of Biological Chemistry, vol. 266(23), pp. 15493-15497, Aug. 15, 1991, The Carboxyl-terminal End of Protective antigen is required for receptor binding and Anthrax toxin activity.*
Iacono-Connors, L et al, Infection and Immunity, vol. 59(6), pp. 1961-1965, Jun. 1991, Protection against Anthrax with recombinant virus expressed Protective Antigen in Experimental Animals.*

(Continued)

*Primary Examiner*—Robert B Mondesi
*Assistant Examiner*—Ginny Portner
(74) *Attorney, Agent, or Firm*—Elizabeth Arwine

(57) ABSTRACT

Using the nontoxic PA protein from *B. anthracis*, a method and composition for use in inducing an immune response which is protective against anthrax in subjects is described.

10 Claims, 5 Drawing Sheets

OTHER PUBLICATIONS

Pushko, Peter et al Virology, vol. 239, pates 389-401, 1997, Replicon-Helper Systems from attenuated Venezuelan Equine Encephalitis Virus:Expression of Heterologous Genes in Vitro and Immunization against Heterologous Pathogens in Vivo.*

Lee, John S e tal, Vanezuelan Equine Encephalitis Virus-Vectored Vaccines Protect Mice against Anthrax Spore Challenge, Infection and Immunity Mar. 2003, vol. 71(3), pp. 1491-1496.*

International Search Report issued Aug. 2, 2000 in related PCT application PCT/US99/15568 (11 pages).

Clayton et al., "Protective Vaccination with a Recombinant Fragment of Clostridium botulinum Neurotoxin Serotype A Expressed from a Synthetic Gene in *E. coli*", Infection and Immunity, Jul. 1995, vol. 63, No. 7, pp. 2738-2742.

Byrne, et al., "Purification, Potency, and Efficacy of the Botulinum Neurotoxin Type A Binding Domain from *Pichia pastoris* as a Recombinant Vaccine Candidate", Infection and Immunity, Oct. 1998, vol. 66, No. 10, pp. 4817-4822.

Pushko, et al., "Replicon-Helper Systems from Attenuated Venezuelan Equine Encephalitis Virus: Expression of Heterologous Genes in Vitro and Immunization against Heterologous Pathogens in Vivo," Virology:239, pp. 389-401 (1997).

Bavari, et al., "Engineered Bacterial Superantigen Vaccines", Vaccines 96, 1996, pp. 135-141.

Welkos et al., "Sequence and analysis of the DNA encoding protective antigen of *Bacillus anthracis*", Gene, 69, 1988, pp. 287-300.

Iocono-Connors et al., "Protection against Anthrax with Recombinant Virus-Expressed Protective Antigen in Experimental Animals", Infection and Immunity, Jun. 1991, pp. 1961-1965.

Singh, et al., "A Deleted Variant of *Bacillus antracix* Protective Antigen is Non-toxic and Blocks Anthrax Toxin Action in Vivo", The Journal of Biological Chemistry, vol. 264, No. 32, pp. 19101-19107, Nov. 15, 1989.

Ivins and Welkos, "Cloning and Expression of the *Bacillus anthracis* Protective Antigen Gene in *Bacillus subtilis*", Infectin and Immunity, vol. 54, No. 2, pp. 537-542 (Nov. 1986).

Orkin et al., "Report and Recommendations of the Panel to Assess the NIH Investment in Research on Gene Therapy", Dec. 1995, pp. 1-41.

Chattergoon et al, FASEB, "Genetic Immunization: A New Era in Vaccines and Immune Therapeutics," May 1997, 11, pp. 753-763.

McDonnell et al., The New England Journal of Medicine, "Molecular Medicine DNA Vaccines", Jan. 1996, vol. 334, No. 1, pp. 42-45.

Ledley, Human Gene Therapy, "Clinical Considerations in the Design of Protocols for Somatic Gene Therapy," 1991, 2:77-83.

Zinkernagel, Fundamental Immunology, "Immunity to Viruses", Chap. 34, 3rd Ed., pp. 1211-1250.

* cited by examiner

C57Bl/6 mice

- ■ 26 days post-1st inoc.
- ▨ 26-28 days post-2nd inoc.
- ▨ 26-28 days post-3rd inoc.
- ▨ 28 days post-4th inoc.

X-axis (survived/total): AVA human vaccine[a] 10/10, Lassa N replicon[b] 0/10, group 1[c] 9/10, group 2[d] 7/10, group 3[e] 3/10

Y-axis: Geometric mean titer (1/dil), $10^2$ to $10^7$

SEQUENCE LISTING

<160> NUMBER OF SEQ ID NOS: 18

<210> SEQ ID NO 1
<211> LENGTH: 2295
<212> TYPE: DNA
<213> ORGANISM: Bacillus anthracis

<400> SEQUENCE: 1

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa tttcaagca      180 cccatggtgg ttacctcttc tactacaggg gatttatcta ttcctagttc tgagttagaa     240
aatattccat cggaaaacca atattttcaa tctgctattt ggtcaggatt tatcaaagtt     300
```

| | |
|---|---|
| aagaagagtg atgaatatac atttgctact tccgctgata atcatgtaac aatgtgggta | 360 |
| gatgaccaag aagtgattaa taaagcttct aattctaaca aaatcagatt agaaaaagga | 420 |
| agattatatc aaataaaaat tcaatatcaa cgagaaaatc ctactgaaaa aggattggat | 480 |
| ttcaagttgt actggaccga ttctcaaaat aaaaagaag tgatttctag tgataactta | 540 |
| caattgccag aattaaaaca aaatcttcg aactcaagaa aaagacaag tacaagtgct | 600 |
| ggacctacgg ttccagaccg tgacaatgat ggaatccctg attcattaga ggtagaagga | 660 |
| tatacggttg atgtcaaaaa taaagaact tttctttcac catggatttc taatattcat | 720 |
| gaaaagaaag gattaaccaa atataaatca tctcctgaaa aatggagcac ggcttctgat | 780 |
| ccgtacagtg atttcgaaaa ggttacagga cggattgata gaatgtatc accagaggca | 840 |
| agacaccccc ttgtggcagc ttatccgatt gtacatgtag atatggagaa tattattctc | 900 |
| tcaaaaaatg aggatcaatc cacacagaat actgatagtg aaacgagaac aataagtaaa | 960 |
| aatacttcta caagtaggac acatactagt gaagtacatg gaaatgcaga agtgcatgcg | 1020 |
| tcgttctttg atattggtgg gagtgtatct gcaggattta gtaattcgaa ttcaagtacg | 1080 |
| gtcgcaattg atcattcact atctctagca ggggaaagaa cttgggctga aacaatgggt | 1140 |
| ttaaataccg ctgatacagc aagattaaat gccaatatta gatatgtaaa tactgggacg | 1200 |
| gctccaatct acaacgtgtt accaacgact tcgttagtgt taggaaaaaa tcaaacactc | 1260 |
| gcgacaatta aagctaagga aaaccaatta agtcaaatac ttgcacctaa taattattat | 1320 |
| ccttctaaaa acttggcgcc aatcgcatta aatgcacaag acgatttcag ttctactcca | 1380 |
| attacaatga attacaatca atttcttgag ttagaaaaaa cgaaacaatt aagattagat | 1440 |
| acggatcaag tatatgggaa tatagcaaca tacaattttg aaaatggaag agtgagggtg | 1500 |
| gatacaggct cgaactggag tgaagtgtta ccgcaaattc aagaaacaac tgcacgtatc | 1560 |
| attttaatg aaaagatt aaatctggta gaaaggcgga tagcggcggt taatcctagt | 1620 |
| gatccattag aaacgactaa accggatatg acattaaaag aagcccttaa aatagcattt | 1680 |
| ggatttaacg aaccgaatgg aaacttacaa tatcaaggga agacataac cgaatttgat | 1740 |
| tttaatttcg atcaacaaac atctcaaaat atcaagaatc agttagcgga attaaacgca | 1800 |
| actaacatat atactgtatt agataaaatc aaattaaatg caaaaatgaa tattttaata | 1860 |
| agagataaac gttttcatta tgatagaaat aacatagcag ttggggcgga tgagtcagta | 1920 |
| gttaaggagg ctcatagaga agtaattaat tcgtcaacag agggattatt gttaaatatt | 1980 |
| gataaggata taagaaaaat attatcaggt tatattgtag aaattgaaga tactgaaggg | 2040 |
| cttaaagaag ttataaatga cagatatgat atgttgaata tttctagttt acggcaagat | 2100 |
| ggaaaaacat ttatagattt taaaaatat aatgataaat taccgttata tataagtaat | 2160 |
| cccaattata aggtaaatgt atatgctgtt actaaagaaa acactattat taatcctagt | 2220 |
| gagaatgggg atactagtac caacgggatc aagaaaattt taatctttc taaaaaaggc | 2280 |
| tatgagatag gataa | 2295 |

<210> SEQ ID NO 2
<211> LENGTH: 2211
<212> TYPE: DNA
<213> ORGANISM: Bacillus anthracis

<400> SEQUENCE: 2

| | |
|---|---|
| atggaagtta acaggagaa ccggttatta aatgaatcag aatcaagttc ccaggggtta | 60 |

```
ctaggatact attttagtga tttgaattt caagcaccca tggtggttac ctcttctact    120 acagggatt tatctattcc tagttctgag ttagaaaata ttccatcgga aaaccaatat    180
tttcaatctg ctatttggtc aggatttatc aaagttaaga gagtgatga atatacattt    240 gctacttccg ctgataatca tgtaacaatg tgggtagatg accaagaagt gattaataaa    300
gcttctaatt ctaacaaaat cagattagaa aaaggaagat tatatcaaat aaaaattcaa    360
tatcaacgag aaaatcctac tgaaaaagga ttggatttca agttgtactg gaccgattct    420
caaaataaaa aagaagtgat ttctagtgat aacttacaat tgccagaatt aaaacaaaaa    480
tcttcgaact caagaaaaaa gcgaagtaca agtgctggac ctacggttcc agaccgtgac    540
aatgatggaa tccctgattc attagaggta gaaggatata cggttgatgt caaaaataaa    600 agaactttc tttcaccatg gatttctaat attcatgaaa agaaaggatt aaccaaatat    660
aaatcatctc ctgaaaaatg gagcacggct tctgatccgt acagtgattt cgaaaaggtt    720
acaggacgga ttgataagaa tgtatcacca gaggcaagac accccttgt ggcagcttat    780 ccgattgtac atgtagatat ggagaatatt attctctcaa aaaatgagga tcaatccaca    840
cagaatactg atagtgaaac gagaacaata agtaaaaata cttctacaag taggacacat    900
actagtgaag tacatggaaa tgcagaagtg catgcgtcgt tcttgatat tggtgggagt    960 gtatctgcag gatttagtaa ttcgaattca agtacggtcg caattgatca ttcactatct   1020
ctagcagggg aaagaacttg gctgaaaca atgggtttaa ataccgctga tacagcaaga   1080
ttaaatgcca atattagata tgtaaatact gggacggctc caatctacaa cgtgttacca   1140
acgacttcgt tagtgttagg aaaaaatcaa acactcgcga caattaaagc taaggaaaac   1200
caattaagtc aaatacttgc acctaataat tattatcctt ctaaaaactt ggcgccaatc   1260
gcattaaatg cacaagacga tttcagttct actccaatta caatgaatta caatcaattt   1320
cttgagttag aaaaaacgaa acaattaaga ttagatacgg atcaagtata tgggaatata   1380
gcaacataca attttgaaaa tggaagagtg agggtggata caggctcgaa ctggagtgaa   1440
gtgttaccgc aaattcaaga aacaactgca cgtatcattt ttaatggaaa agattaaat   1500 ctggtagaaa ggcggatagc ggcggttaat cctagtgatc cattagaaac gactaaaccg   1560
gatatgacat aaagaagc ccttaaaata gcatttggat ttaacgaacc gaatggaaac   1620
ttacaatatc aagggaaaga cataaccgaa tttgatttta atttcgatca acaaacatct   1680
caaaatatca agaatcagtt agcggaatta aacgcaacta acatatatac tgtattagat   1740 aaaatcaat taaatgcaaa aatgaatatt ttaataagag ataaacgttt tcattatgat   1800
agaaataaca tagcagttgg ggcggatgag tcagtagtta aggaggctca tagagaagta   1860
attaattcgt caacagaggg attattgtta aatattgata aggatataag aaaaatatta   1920
tcaggttata ttgtagaaat tgaagatact gaagggctta agaagttat aaatgacaga   1980 tatgatatgt tgaatatttc tagtttacgg caagatggaa aaacatttat agattttaaa   2040
aaatataatg ataaattacc gttatatata agtaatccca attataaggt aaatgtatat   2100
gctgttacta agaaaaacac tattattaat cctagtgaga atggggatac tagtaccaac   2160
gggatcaaga aaatttaat cttttctaaa aaaggctatg agataggata a              2211
```

<210> SEQ ID NO 3
<211> LENGTH: 2292
<212> TYPE: DNA
<213> ORGANISM: Bacillus anthracis

<400> SEQUENCE: 3

-continued

```
atggatgcaa tgaagagagg gctctgctgt gtgctgctgc tgtgtggagc agtcttcgtt      60
tcggctagcg aggtgattca ggcagaagtt aaacaggaga accggttatt aaatgaatca     120
gaatcaagtt cccaggggtt actaggatac tattttagtg atttgaattt tcaagcaccc     180
atggtggtta cctcttctac tacaggggat ttatctattc ctagttctga gttagaaaat     240
attccatcgg aaaaccaata ttttcaatct gctatttggt caggatttat caaagttaag     300
aagagtgatg aatatacatt tgctacttcc gctgataatc atgtaacaat gtgggtagat     360
gaccaagaag tgattaataa agcttctaat tctaacaaaa tcagattaga aaaggaaga     420
ttatatcaaa taaaaattca atatcaacga gaaaatccta ctgaaaaagg attggatttc     480
aagttgtact ggaccgattc tcaaaataaa aagaagtga tttctagtga taacttacaa      540
ttgccagaat taaaacaaaa atcttcgaac tcaagaaaaa agcgaagtac aagtgctgga     600
cctacggttc cagaccgtga caatgatgga atccctgatt cattagaggt agaaggatat     660
acggttgatg tcaaaaataa aagaactttt ctttcaccat ggatttctaa tattcatgaa     720
aagaaaggat taaccaaata taaatcatct cctgaaaaat ggagcacggc ttctgatccg     780
tacagtgatt tcgaaaaggt tacaggacgg attgataaga atgtatcacc agaggcaaga     840
caccccttg tggcagctta tccgattgta catgtagata tggagaatat tattctctca     900
aaaaatgagg atcaatccac acagaatact gatagtgaaa cgaacaat aagtaaaaat     960
acttctacaa gtaggacaca tactagtgaa gtacatggaa atgcagaagt gcatgcgtcg    1020
ttctttgata ttggtgggag tgtatctgca ggatttagta attcgaattc aagtacggtc    1080
gcaattgatc attcactatc tctagcaggg gaaagaactt gggctgaaac aatgggttta    1140
aataccgctg atacagcaag attaaatgcc aatattgat atgtaaatac tgggacggct    1200
ccaatctaca acgtgttacc aacgacttcg ttagtgttag gaaaaaatca aacactcgcg    1260
acaattaaag ctaaggaaaa ccaattaagt caaatacttg cacctaataa ttattatcct    1320
tctaaaaact tggcgccaat cgcattaaat gcacaagacg atttcagttc tactccaatt    1380
acaatgaatt acaatcaatt tcttgagtta gaaaaaacga aacaattaag attagatacg    1440
gatcaagtat atgggaatat agcaacatac aattttgaaa atggaagagt gagggtggat    1500
acaggctcga actggagtga agtgttaccg caaattcaag aaacaactgc acgtatcatt    1560
tttaatggaa aagatttaaa tctggtagaa aggcggatag cggcggttaa tcctagtgat    1620
ccattagaaa cgactaaacc ggatatgaca ttaaaagaag cccttaaaat agcatttgga    1680
tttaacgaac cgaatggaaa cttacaatat caagggaaag acataaccga atttgatttt    1740
aatttcgatc aacaaacatc tcaaaatatc aagaatcagt tagcggaatt aaacgcaact    1800
aacatatata ctgtattaga taaaatcaaa ttaaatgcaa aaatgaatat tttaataaga    1860
gataaacgtt ttcattatga tagaaataac atagcagttg gggcggatga gtcagtagtt    1920
aaggaggctc atagagaagt aattaattcg tcaacagagg gattattgtt aaatattgat    1980
aaggatataa gaaaaatatt atcaggttat attgtagaaa ttgaagatac tgaagggctt    2040
aaagaagtta taaatgacag atatgatatg ttgaatattt ctagtttacg gcaagatgga    2100
aaaacatttta tagattttaa aaaatataat gataaaattac cgttatatat aagtaatccc    2160
aattataagg taaatgtata tgctgttact aaagaaaaca ctattattaa tcctagtgag    2220
aatggggata ctagtaccaa cgggatcaag aaaattttaa tcttttctaa aaaaggctat    2280
gagataggat aa                                                        2292
```

-continued

<210> SEQ ID NO 4
<211> LENGTH: 1710
<212> TYPE: DNA
<213> ORGANISM: Bacillus anthracis

<400> SEQUENCE: 4

| | |
|---|---|
| atgagtacaa gtgctggacc tacggttcca gaccgtgaca atgatggaat ccctgattca | 60 |
| ttagaggtag aaggatatac ggttgatgtc aaaaataaaa gaactttct ttcaccatgg | 120 |
| atttctaata ttcatgaaaa gaaaggatta accaaatata atcatctcc tgaaaaatgg | 180 |
| agcacggctt ctgatccgta cagtgatttc gaaaaggtta caggacggat tgataagaat | 240 |
| gtatcaccag aggcaagaca ccccttgtg gcagcttatc cgattgtaca tgtagatatg | 300 |
| gagaatatta ttctctcaaa aaatgaggat caatccacac agaatactga tagtgaaacg | 360 |
| agaacaataa gtaaaaatac ttctacaagt aggacacata ctagtgaagt acatggaaat | 420 |
| gcagaagtgc atgcgtcgtt ctttgatatt ggtgggagtg tatctgcagg atttagtaat | 480 |
| tcgaattcaa gtacggtcgc aattgatcat tcactatctc tagcagggga agaacttgg | 540 |
| gctgaaacaa tgggtttaaa taccgctgat acagcaagat aaatgccaa tattagatat | 600 |
| gtaaatactg gacggctcc aatctacaac gtgttaccaa cgacttcgtt agtgttagga | 660 |
| aaaaatcaaa cactcgcgac aattaaagct aaggaaaacc aattaagtca atacttgca | 720 |
| cctaataatt attatccttc taaaaacttg gcgccaatcg cattaaatgc acaagacgat | 780 |
| ttcagttcta ctccaattac aatgaattac aatcaatttc ttgagttaga aaaaacgaaa | 840 |
| caattaagat tagatacgga tcaagtatat gggaatatag caacatacaa ttttgaaaat | 900 |
| ggaagagtga gggtggatac aggctcgaac tggagtgaag tgttaccgca aattcaagaa | 960 |
| acaactgcac gtatcatttt taatggaaaa gatttaaatc tggtagaaag gcggatagcg | 1020 |
| gcggttaatc ctagtgatcc attagaaacg actaaaccgg atatgacatt aaaagaagcc | 1080 |
| cttaaaatag catttggatt taacgaaccg aatggaaact acaatatca agggaaagac | 1140 |
| ataaccgaat tgattttaa tttcgatcaa caaacatctc aaaatatcaa gaatcagtta | 1200 |
| gcggaattaa acgcaactaa catatatact gtattagata aatcaaatt aaatgcaaaa | 1260 |
| atgaatattt taataagaga taaacgttt cattatgata gaaataacat agcagttggg | 1320 |
| gcggatgagt cagtagttaa ggaggctcat agagaagtaa ttaattcgtc aacagaggga | 1380 |
| ttattgttaa atattgataa ggatataaga aaaatattat caggttatat tgtagaaatt | 1440 |
| gaagatactg aagggcttaa agaagttata atgacagat atgatatgtt gaatatttct | 1500 |
| agtttacggc aagatggaaa acatttata gattttaaaa aatataatga taaattaccg | 1560 |
| ttatatataa gtaatcccaa ttataaggta aatgtatatg ctgttactaa agaaaacact | 1620 |
| attattaatc ctagtgagaa tggggatact agtaccaacg ggatcaagaa aattttaatc | 1680 |
| ttttctaaaa aaggctatga gataggataa | 1710 |

<210> SEQ ID NO 5
<211> LENGTH: 763
<212> TYPE: PRT
<213> ORGANISM: Bacillus anthracis

<400> SEQUENCE: 5

Met Asp Ala Met Lys Arg Gly Leu Cys Cys Val Leu Leu Leu Cys Gly
1               5                   10                  15

Ala Val Phe Val Ser Ala Ser Glu Val Ile Gln Ala Glu Val Lys Gln
            20                  25                  30

-continued

```
Glu Asn Arg Leu Leu Asn Glu Ser Glu Ser Ser Gln Gly Leu Leu
         35                  40                  45

Gly Tyr Tyr Phe Ser Asp Leu Asn Phe Gln Ala Pro Met Val Val Thr
 50                  55                  60

Ser Ser Thr Thr Gly Asp Leu Ser Ile Pro Ser Ser Glu Leu Glu Asn
 65                  70                  75                  80

Ile Pro Ser Glu Asn Gln Tyr Phe Gln Ser Ala Ile Trp Ser Gly Phe
                 85                  90                  95

Ile Lys Val Lys Lys Ser Asp Glu Tyr Thr Phe Ala Thr Ser Ala Asp
                100                 105                 110

Asn His Val Thr Met Trp Val Asp Asp Gln Glu Val Ile Asn Lys Ala
                115                 120                 125

Ser Asn Ser Asn Lys Ile Arg Leu Glu Lys Gly Arg Leu Tyr Gln Ile
        130                 135                 140

Lys Ile Gln Tyr Gln Arg Glu Asn Pro Thr Glu Lys Gly Leu Asp Phe
145                 150                 155                 160

Lys Leu Tyr Trp Thr Asp Ser Gln Asn Lys Lys Glu Val Ile Ser Ser
                165                 170                 175

Asp Asn Leu Gln Leu Pro Glu Leu Lys Gln Lys Ser Ser Asn Ser Arg
                180                 185                 190

Lys Lys Arg Ser Thr Ser Ala Gly Pro Thr Val Pro Asp Arg Asp Asn
        195                 200                 205

Asp Gly Ile Pro Asp Ser Leu Glu Val Glu Gly Tyr Thr Val Asp Val
        210                 215                 220

Lys Asn Lys Arg Thr Phe Leu Ser Pro Trp Ile Ser Asn Ile His Glu
225                 230                 235                 240

Lys Lys Gly Leu Thr Lys Tyr Lys Ser Ser Pro Glu Lys Trp Ser Thr
                245                 250                 255

Ala Ser Asp Pro Tyr Ser Asp Phe Glu Lys Val Thr Gly Arg Ile Asp
                260                 265                 270

Lys Asn Val Ser Pro Glu Ala Arg His Pro Leu Val Ala Ala Tyr Pro
        275                 280                 285

Ile Val His Val Asp Met Glu Asn Ile Ile Leu Ser Lys Asn Glu Asp
        290                 295                 300

Gln Ser Thr Gln Asn Thr Asp Ser Glu Thr Arg Thr Ile Ser Lys Asn
305                 310                 315                 320

Thr Ser Thr Ser Arg Thr His Thr Ser Glu Val His Gly Asn Ala Glu
                325                 330                 335

Val His Ala Ser Phe Phe Asp Ile Gly Gly Ser Val Ser Ala Gly Phe
                340                 345                 350

Ser Asn Ser Asn Ser Ser Thr Val Ala Ile Asp His Ser Leu Ser Leu
        355                 360                 365

Ala Gly Glu Arg Thr Trp Ala Glu Thr Met Gly Leu Asn Thr Ala Asp
        370                 375                 380

Thr Ala Arg Leu Asn Ala Asn Ile Arg Tyr Val Asn Thr Gly Thr Ala
385                 390                 395                 400

Pro Ile Tyr Asn Val Leu Pro Thr Thr Ser Leu Val Leu Gly Lys Asn
                405                 410                 415

Gln Thr Leu Ala Thr Ile Lys Ala Lys Glu Asn Gln Leu Ser Gln Ile
                420                 425                 430

Leu Ala Pro Asn Asn Tyr Tyr Pro Ser Lys Asn Leu Ala Pro Ile Ala
        435                 440                 445
```

```
Leu Asn Ala Gln Asp Asp Phe Ser Ser Thr Pro Ile Thr Met Asn Tyr
    450                 455                 460

Asn Gln Phe Leu Glu Leu Glu Lys Thr Lys Gln Leu Arg Leu Asp Thr
465                 470                 475                 480

Asp Gln Val Tyr Gly Asn Ile Ala Thr Tyr Asn Phe Glu Asn Gly Arg
                485                 490                 495

Val Arg Val Asp Thr Gly Ser Asn Trp Ser Glu Val Leu Pro Gln Ile
            500                 505                 510

Gln Glu Thr Thr Ala Arg Ile Ile Phe Asn Gly Lys Asp Leu Asn Leu
        515                 520                 525

Val Glu Arg Arg Ile Ala Ala Val Asn Pro Ser Asp Pro Leu Glu Thr
    530                 535                 540

Thr Lys Pro Asp Met Thr Leu Lys Glu Ala Leu Lys Ile Ala Phe Gly
545                 550                 555                 560

Phe Asn Glu Pro Asn Gly Asn Leu Gln Tyr Gln Gly Lys Asp Ile Thr
                565                 570                 575

Glu Phe Asp Phe Asn Phe Asp Gln Gln Thr Ser Gln Asn Ile Lys Asn
            580                 585                 590

Gln Leu Ala Glu Leu Asn Ala Thr Asn Ile Tyr Thr Val Leu Asp Lys
        595                 600                 605

Ile Lys Leu Asn Ala Lys Met Asn Ile Leu Ile Arg Asp Lys Arg Phe
    610                 615                 620

His Tyr Asp Arg Asn Asn Ile Ala Val Gly Ala Asp Glu Ser Val Val
625                 630                 635                 640

Lys Glu Ala His Arg Glu Val Ile Asn Ser Ser Thr Glu Gly Leu Leu
                645                 650                 655

Leu Asn Ile Asp Lys Asp Ile Arg Lys Ile Leu Ser Gly Tyr Ile Val
            660                 665                 670

Glu Ile Glu Asp Thr Glu Gly Leu Lys Glu Val Ile Asn Asp Arg Tyr
        675                 680                 685

Asp Met Leu Asn Ile Ser Ser Leu Arg Gln Asp Gly Lys Thr Phe Ile
    690                 695                 700

Asp Phe Lys Lys Tyr Asn Asp Lys Leu Pro Leu Tyr Ile Ser Asn Pro
705                 710                 715                 720

Asn Tyr Lys Val Asn Val Tyr Ala Val Thr Lys Glu Asn Thr Ile Ile
                725                 730                 735

Asn Pro Ser Glu Asn Gly Asp Thr Ser Thr Asn Gly Ile Lys Lys Ile
            740                 745                 750

Leu Ile Phe Ser Lys Lys Gly Tyr Glu Ile Gly
        755                 760

<210> SEQ ID NO 6
<211> LENGTH: 764
<212> TYPE: PRT
<213> ORGANISM: Bacillus anthracis

<400> SEQUENCE: 6

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60
```

-continued

```
Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Gln Glu Val Ile Asn Lys
            115                 120                 125

Ala Ser Asn Ser Asn Lys Ile Arg Leu Glu Lys Gly Arg Leu Tyr Gln
130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
            195                 200                 205

Asn Asp Gly Ile Pro Asp Ser Leu Glu Val Glu Gly Tyr Thr Val Asp
210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
            275                 280                 285

Pro Ile Val His Val Asp Met Glu Asn Ile Ile Leu Ser Lys Asn Glu
290                 295                 300

Asp Gln Ser Thr Gln Asn Thr Asp Ser Glu Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
            355                 360                 365

Leu Ala Gly Glu Arg Thr Trp Ala Glu Thr Met Gly Leu Asn Thr Ala
370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480
```

```
Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
            530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
            595                 600                 605

Lys Ile Lys Leu Asn Ala Lys Met Asn Ile Leu Ile Arg Asp Lys Arg
610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
            645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
            675                 680                 685

Tyr Asp Met Leu Asn Ile Ser Ser Leu Arg Gln Asp Gly Lys Thr Phe
            690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
                740                 745                 750

Ile Leu Ile Phe Ser Lys Lys Gly Tyr Glu Ile Gly
                755                 760

<210> SEQ ID NO 7
<211> LENGTH: 736
<212> TYPE: PRT
<213> ORGANISM: Bacillus anthracis

<400> SEQUENCE: 7

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
                20                  25                  30

Pro Met Val Val Thr Ser Ser Thr Thr Gly Asp Leu Ser Ile Pro Ser
            35                  40                  45

Ser Glu Leu Glu Asn Ile Pro Ser Glu Asn Gln Tyr Phe Gln Ser Ala
        50                  55                  60

Ile Trp Ser Gly Phe Ile Lys Val Lys Lys Ser Asp Glu Tyr Thr Phe
65              70                  75                  80

Ala Thr Ser Ala Asp Asn His Val Thr Met Trp Val Asp Asp Gln Glu
                85                  90                  95
```

-continued

```
Val Ile Asn Lys Ala Ser Asn Ser Asn Lys Ile Arg Leu Glu Lys Gly
                100                 105                 110
Arg Leu Tyr Gln Ile Lys Ile Gln Tyr Gln Arg Glu Asn Pro Thr Glu
            115                 120                 125
Lys Gly Leu Asp Phe Lys Leu Tyr Trp Thr Asp Ser Gln Asn Lys Lys
        130                 135                 140
Glu Val Ile Ser Ser Asp Asn Leu Gln Leu Pro Glu Leu Lys Gln Lys
145                 150                 155                 160
Ser Ser Asn Ser Arg Lys Lys Arg Ser Thr Ser Ala Gly Pro Thr Val
                165                 170                 175
Pro Asp Arg Asp Asn Asp Gly Ile Pro Asp Ser Leu Glu Val Glu Gly
            180                 185                 190
Tyr Thr Val Asp Val Lys Asn Lys Arg Thr Phe Leu Ser Pro Trp Ile
        195                 200                 205
Ser Asn Ile His Glu Lys Lys Gly Leu Thr Lys Tyr Lys Ser Ser Pro
210                 215                 220
Glu Lys Trp Ser Thr Ala Ser Asp Pro Tyr Ser Asp Phe Glu Lys Val
225                 230                 235                 240
Thr Gly Arg Ile Asp Lys Asn Val Ser Pro Glu Ala Arg His Pro Leu
                245                 250                 255
Val Ala Ala Tyr Pro Ile Val His Val Asp Met Glu Asn Ile Ile Leu
            260                 265                 270
Ser Lys Asn Glu Asp Gln Ser Thr Gln Asn Thr Asp Ser Glu Thr Arg
        275                 280                 285
Thr Ile Ser Lys Asn Thr Ser Thr Ser Arg Thr His Thr Ser Glu Val
        290                 295                 300
His Gly Asn Ala Glu Val His Ala Ser Phe Phe Asp Ile Gly Gly Ser
305                 310                 315                 320
Val Ser Ala Gly Phe Ser Asn Ser Asn Ser Ser Thr Val Ala Ile Asp
                325                 330                 335
His Ser Leu Ser Leu Ala Gly Glu Arg Thr Trp Ala Glu Thr Met Gly
            340                 345                 350
Leu Asn Thr Ala Asp Thr Ala Arg Leu Asn Ala Asn Ile Arg Tyr Val
        355                 360                 365
Asn Thr Gly Thr Ala Pro Ile Tyr Asn Val Leu Pro Thr Thr Ser Leu
    370                 375                 380
Val Leu Gly Lys Asn Gln Thr Leu Ala Thr Ile Lys Ala Lys Glu Asn
385                 390                 395                 400
Gln Leu Ser Gln Ile Leu Ala Pro Asn Asn Tyr Tyr Pro Ser Lys Asn
                405                 410                 415
Leu Ala Pro Ile Ala Leu Asn Ala Gln Asp Asp Phe Ser Ser Thr Pro
            420                 425                 430
Ile Thr Met Asn Tyr Asn Gln Phe Leu Glu Leu Glu Lys Thr Lys Gln
        435                 440                 445
Leu Arg Leu Asp Thr Asp Gln Val Tyr Gly Asn Ile Ala Thr Tyr Asn
    450                 455                 460
Phe Glu Asn Gly Arg Val Arg Val Asp Thr Gly Ser Asn Trp Ser Glu
465                 470                 475                 480
Val Leu Pro Gln Ile Gln Glu Thr Thr Ala Arg Ile Ile Phe Asn Gly
                485                 490                 495
Lys Asp Leu Asn Leu Val Glu Arg Arg Ile Ala Ala Val Asn Pro Ser
            500                 505                 510
```

```
Asp Pro Leu Glu Thr Thr Lys Pro Asp Met Thr Leu Lys Glu Ala Leu
            515                 520                 525

Lys Ile Ala Phe Gly Phe Asn Glu Pro Asn Gly Asn Leu Gln Tyr Gln
        530                 535                 540

Gly Lys Asp Ile Thr Glu Phe Asp Phe Asn Phe Asp Gln Gln Thr Ser
545                 550                 555                 560

Gln Asn Ile Lys Asn Gln Leu Ala Glu Leu Asn Ala Thr Asn Ile Tyr
                565                 570                 575

Thr Val Leu Asp Lys Ile Lys Leu Asn Ala Lys Met Asn Ile Leu Ile
            580                 585                 590

Arg Asp Lys Arg Phe His Tyr Asp Arg Asn Asn Ile Ala Val Gly Ala
        595                 600                 605

Asp Glu Ser Val Val Lys Glu Ala His Arg Glu Val Ile Asn Ser Ser
    610                 615                 620

Thr Glu Gly Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
                645                 650                 655

Ile Asn Asp Arg Tyr Asp Met Leu Asn Ile Ser Ser Leu Arg Gln Asp
            660                 665                 670

Gly Lys Thr Phe Ile Asp Phe Lys Lys Tyr Asn Asp Lys Leu Pro Leu
        675                 680                 685

Tyr Ile Ser Asn Pro Asn Tyr Lys Val Asn Val Tyr Ala Val Thr Lys
    690                 695                 700

Glu Asn Thr Ile Ile Asn Pro Ser Glu Asn Gly Asp Thr Ser Thr Asn
705                 710                 715                 720

Gly Ile Lys Lys Ile Leu Ile Phe Ser Lys Lys Gly Tyr Glu Ile Gly
                725                 730                 735

<210> SEQ ID NO 8
<211> LENGTH: 569
<212> TYPE: PRT
<213> ORGANISM: Bacillus anthracis

<400> SEQUENCE: 8

Met Ser Thr Ser Ala Gly Pro Thr Val Pro Asp Arg Asp Asn Asp Gly
1               5                   10                  15

Ile Pro Asp Ser Leu Glu Val Glu Gly Tyr Thr Val Asp Val Lys Asn
                20                  25                  30

Lys Arg Thr Phe Leu Ser Pro Trp Ile Ser Asn Ile His Glu Lys Lys
            35                  40                  45

Gly Leu Thr Lys Tyr Lys Ser Ser Pro Glu Lys Trp Ser Thr Ala Ser
        50                  55                  60

Asp Pro Tyr Ser Asp Phe Glu Lys Val Thr Gly Arg Ile Asp Lys Asn
65                  70                  75                  80

Val Ser Pro Glu Ala Arg His Pro Leu Val Ala Ala Tyr Pro Ile Val
                85                  90                  95

His Val Asp Met Glu Asn Ile Ile Leu Ser Lys Asn Glu Asp Gln Ser
            100                 105                 110

Thr Gln Asn Thr Asp Ser Glu Thr Arg Thr Ile Ser Lys Asn Thr Ser
        115                 120                 125

Thr Ser Arg Thr His Thr Ser Glu Val His Gly Asn Ala Glu Val His
    130                 135                 140

Ala Ser Phe Phe Asp Ile Gly Gly Ser Val Ser Ala Gly Phe Ser Asn
145                 150                 155                 160
```

```
Ser Asn Ser Ser Thr Val Ala Ile Asp His Ser Leu Ser Leu Ala Gly
            165                 170                 175

Glu Arg Thr Trp Ala Glu Thr Met Gly Leu Asn Thr Ala Asp Thr Ala
            180                 185                 190

Arg Leu Asn Ala Asn Ile Arg Tyr Val Asn Thr Gly Thr Ala Pro Ile
            195                 200                 205

Tyr Asn Val Leu Pro Thr Thr Ser Leu Val Leu Gly Lys Asn Gln Thr
            210                 215                 220

Leu Ala Thr Ile Lys Ala Lys Glu Asn Gln Leu Ser Gln Ile Leu Ala
225                 230                 235                 240

Pro Asn Asn Tyr Tyr Pro Ser Lys Asn Leu Ala Pro Ile Ala Leu Asn
            245                 250                 255

Ala Gln Asp Asp Phe Ser Ser Thr Pro Ile Thr Met Asn Tyr Asn Gln
            260                 265                 270

Phe Leu Glu Leu Glu Lys Thr Lys Gln Leu Arg Leu Asp Thr Asp Gln
            275                 280                 285

Val Tyr Gly Asn Ile Ala Thr Tyr Asn Phe Glu Asn Gly Arg Val Arg
            290                 295                 300

Val Asp Thr Gly Ser Asn Trp Ser Glu Val Leu Pro Gln Ile Gln Glu
305                 310                 315                 320

Thr Thr Ala Arg Ile Ile Phe Asn Gly Lys Asp Leu Asn Leu Val Glu
            325                 330                 335

Arg Arg Ile Ala Ala Val Asn Pro Ser Asp Pro Leu Glu Thr Thr Lys
            340                 345                 350

Pro Asp Met Thr Leu Lys Glu Ala Leu Lys Ile Ala Phe Gly Phe Asn
            355                 360                 365

Glu Pro Asn Gly Asn Leu Gln Tyr Gln Gly Lys Asp Ile Thr Glu Phe
            370                 375                 380

Asp Phe Asn Phe Asp Gln Gln Thr Ser Gln Asn Ile Lys Asn Gln Leu
385                 390                 395                 400

Ala Glu Leu Asn Ala Thr Asn Ile Tyr Thr Val Leu Asp Lys Ile Lys
            405                 410                 415

Leu Asn Ala Lys Met Asn Ile Leu Ile Arg Asp Lys Arg Phe His Tyr
            420                 425                 430

Asp Arg Asn Asn Ile Ala Val Gly Ala Asp Glu Ser Val Val Lys Glu
            435                 440                 445

Ala His Arg Glu Val Ile Asn Ser Ser Thr Glu Gly Leu Leu Leu Asn
            450                 455                 460

Ile Asp Lys Asp Ile Arg Lys Ile Leu Ser Gly Tyr Ile Val Glu Ile
465                 470                 475                 480

Glu Asp Thr Glu Gly Leu Lys Glu Val Ile Asn Asp Arg Tyr Asp Met
            485                 490                 495

Leu Asn Ile Ser Ser Leu Arg Gln Asp Gly Lys Thr Phe Ile Asp Phe
            500                 505                 510

Lys Lys Tyr Asn Asp Lys Leu Pro Leu Tyr Ile Ser Asn Pro Asn Tyr
            515                 520                 525

Lys Val Asn Val Tyr Ala Val Thr Lys Glu Asn Thr Ile Ile Asn Pro
            530                 535                 540

Ser Glu Asn Gly Asp Thr Ser Thr Asn Gly Ile Lys Lys Ile Leu Ile
545                 550                 555                 560

Phe Ser Lys Lys Gly Tyr Glu Ile Gly
            565
```

<210> SEQ ID NO 9
<211> LENGTH: 504
<212> TYPE: DNA
<213> ORGANISM: Bacillus anthracis

<400> SEQUENCE: 9

| | | | | | |
|---|---|---|---|---|---|
| atggaagtta | aacaggagaa | ccggttatta | aatgaatcag | aatcaagttc | ccagggg tta | 60 |
| ctaggatact | attttagtga | tttgaatttt | caagcaccca | tggtggttac | ctcttctact | 120 |
| acagggg att | tatctattcc | tagttctgag | ttagaaaata | ttccatcgga | aaaccaatat | 180 |
| tttcaatctg | ctatttggtc | aggatttatc | aaagttaaga | gagtgatga | atatacattt | 240 |
| gctacttccg | ctgataatca | tgtaacaatg | tgggtagatg | accaagaagt | gattaataaa | 300 |
| gcttctaatt | ctaacaaaat | cagattagaa | aaggaagat | tatatcaaat | aaaaattcaa | 360 |
| tatcaacgag | aaaatcctac | tgaaaaagga | ttggatttca | agttgtactg | gaccgattct | 420 |
| caaaataaaa | aagaagtgat | tctagtgat | aacttacaat | tgccagaatt | aaaacaaaaa | 480 |
| tcttcgaact | caagaaaaaa | gcga | | | | 504 |

<210> SEQ ID NO 10
<211> LENGTH: 168
<212> TYPE: PRT
<213> ORGANISM: Bacillus anthracis

<400> SEQUENCE: 10

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30

Pro Met Val Val Thr Ser Ser Thr Gly Asp Leu Ser Ile Pro Ser
        35                  40                  45

Ser Glu Leu Glu Asn Ile Pro Ser Glu Asn Gln Tyr Phe Gln Ser Ala
    50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
    130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg
                165

<210> SEQ ID NO 11
<211> LENGTH: 267
<212> TYPE: DNA
<213> ORGANISM: Bacillus anthracis

<400> SEQUENCE: 11

| | | | | | |
|---|---|---|---|---|---|
| agtacaagtg | ctggacctac | ggttccagac | cgtgacaatg | atggaatccc | tgattcatta | 60 |
| gaggtagaag | gatatacggt | tgatgtcaaa | aataaaagaa | cttttctttc | accatggatt | 120 |

```
tctaatattc atgaaaagaa aggattaacc aaatataaat catctcctga aaaatggagc      180
acggcttctg atccgtacag tgatttcgaa aaggttacag acggattga taagaatgta       240 tcaccagagg caagacaccc ccttgtg                                          267
```

<210> SEQ ID NO 12
<211> LENGTH: 89
<212> TYPE: PRT
<213> ORGANISM: Bacillus anthracis

<400> SEQUENCE: 12

```
Ser Thr Ser Ala Gly Pro Thr Val Pro Asp Arg Asp Asn Asp Gly Ile
 1               5                  10                  15

Pro Asp Ser Leu Glu Val Glu Gly Tyr Thr Val Asp Val Lys Asn Lys
                20                  25                  30

Arg Thr Phe Leu Ser Pro Trp Ile Ser Asn Ile His Glu Lys Lys Gly
         35                  40                  45

Leu Thr Lys Tyr Lys Ser Ser Pro Glu Lys Trp Ser Thr Ala Ser Asp
     50                  55                  60

Pro Tyr Ser Asp Phe Glu Lys Val Thr Gly Arg Ile Asp Lys Asn Val
 65                  70                  75                  80

Ser Pro Glu Ala Arg His Pro Leu Val
                 85
```

<210> SEQ ID NO 13
<211> LENGTH: 693
<212> TYPE: DNA
<213> ORGANISM: Bacillus anthracis

<400> SEQUENCE: 13

```
gcagcttatc cgattgtaca tgtagatatg gagaatatta ttctctcaaa aaatgaggat      60
caatccacac agaatactga tagtgaaacg agaacaataa gtaaaaatac ttctacaagt     120
aggacacata ctagtgaagt acatggaaat gcagaagtgc atgcgtcgtt ctttgatatt     180
ggtgggagtg tatctgcagg atttagtaat tcgaattcaa gtacggtcgc aattgatcat     240
tcactatctc tagcagggga agaacttggg gctgaaacaa tgggtttaaa taccgctgat     300
acagcaagat taaatgccaa tattagatat gtaaatactg ggacggctcc aatctacaac     360
gtgttaccaa cgacttcgtt agtgttagga aaaaatcaaa cactcgcgac aattaaagct     420
aaggaaaacc aattaagtca atacttgca cctaataatt attatccttc taaaaacttg      480
gcgccaatcg cattaaatgc acaagacgat ttcagttcta ctccaattac aatgaattac     540
aatcaatttc ttgagttaga aaaaacgaaa caattaagat tagatacgga tcaagtatat     600
gggaatatag caacatacaa ttttgaaaat ggaagagtga gggtggatac aggctcgaac     660
tggagtgaag tgttaccgca aattcaagaa aca                                  693
```

<210> SEQ ID NO 14
<211> LENGTH: 231
<212> TYPE: PRT
<213> ORGANISM: Bacillus anthracis

<400> SEQUENCE: 14

```
Ala Ala Tyr Pro Ile Val His Val Asp Met Glu Asn Ile Ile Leu Ser
 1               5                  10                  15

Lys Asn Glu Asp Gln Ser Thr Gln Asn Thr Asp Ser Glu Thr Arg Thr
                20                  25                  30

Ile Ser Lys Asn Thr Ser Thr Ser Arg Thr His Thr Ser Glu Val His
```

-continued

```
                35                   40                  45
Gly Asn Ala Glu Val His Ala Ser Phe Phe Asp Ile Gly Gly Ser Val
 50                  55                  60

Ser Ala Gly Phe Ser Asn Ser Asn Ser Ser Thr Val Ala Ile Asp His
 65                  70                  75                  80

Ser Leu Ser Leu Ala Gly Glu Arg Thr Trp Ala Glu Thr Met Gly Leu
                 85                  90                  95

Asn Thr Ala Asp Thr Ala Arg Leu Asn Ala Asn Ile Arg Tyr Val Asn
                100                 105                 110

Thr Gly Thr Ala Pro Ile Tyr Asn Val Leu Pro Thr Thr Ser Leu Val
            115                 120                 125

Leu Gly Lys Asn Gln Thr Leu Ala Thr Ile Lys Ala Lys Glu Asn Gln
130                 135                 140

Leu Ser Gln Ile Leu Ala Pro Asn Asn Tyr Tyr Pro Ser Lys Asn Leu
145                 150                 155                 160

Ala Pro Ile Ala Leu Asn Ala Gln Asp Asp Phe Ser Ser Thr Pro Ile
                165                 170                 175

Thr Met Asn Tyr Asn Gln Phe Leu Glu Leu Glu Lys Thr Lys Gln Leu
                180                 185                 190

Arg Leu Asp Thr Asp Gln Val Tyr Gly Asn Ile Ala Thr Tyr Asn Phe
            195                 200                 205

Glu Asn Gly Arg Val Arg Val Asp Thr Gly Ser Asn Trp Ser Glu Val
    210                 215                 220

Leu Pro Gln Ile Gln Glu Thr
225                 230

<210> SEQ ID NO 15
<211> LENGTH: 318
<212> TYPE: DNA
<213> ORGANISM: Bacillus anthracis

<400> SEQUENCE: 15
actgcacgta tcattttta atggaaaagat ttaaatctgg tagaaaggcg gatagcggcg    60
gttaatccta gtgatccatt agaaacgact aaaccggata tgacattaaa agaagccctt   120
aaaatagcat ttggatttaa cgaaccgaat ggaaacttac aatatcaagg gaaagacata   180
accgaatttg attttaattt cgatcaacaa acatctcaaa atatcaagaa tcagttagcg   240
gaattaaacg caactaacat atatactgta ttagataaaa tcaaattaaa tgcaaaaatg   300
aatattttta taagagat                                                 318

<210> SEQ ID NO 16
<211> LENGTH: 106
<212> TYPE: PRT
<213> ORGANISM: Bacillus anthracis

<400> SEQUENCE: 16

Thr Ala Arg Ile Ile Phe Asn Gly Lys Asp Leu Asn Leu Val Glu Arg
  1               5                  10                  15

Arg Ile Ala Ala Val Asn Pro Ser Asp Pro Leu Glu Thr Thr Lys Pro
                 20                  25                  30

Asp Met Thr Leu Lys Glu Ala Leu Lys Ile Ala Phe Gly Phe Asn Glu
            35                  40                  45

Pro Asn Gly Asn Leu Gln Tyr Gln Gly Lys Asp Ile Thr Glu Phe Asp
     50                  55                  60

Phe Asn Phe Asp Gln Gln Thr Ser Gln Asn Ile Lys Asn Gln Leu Ala
```

```
                           65                  70                  75                  80
Glu Leu Asn Ala Thr Asn Ile Tyr Thr Val Leu Asp Lys Ile Lys Leu
                    85                  90                  95

Asn Ala Lys Met Asn Ile Leu Ile Arg Asp
                100                 105

<210> SEQ ID NO 17
<211> LENGTH: 429
<212> TYPE: DNA
<213> ORGANISM: Bacillus anthracis

<400> SEQUENCE: 17
aaacgttttc attatgatag aaataacata gcagttgggg cggatgagtc agtagttaag      60
gaggctcata gagaagtaat taattcgtca acagagggat tattgttaaa tattgataag     120
gatataagaa aaatattatc aggttatatt gtagaaattg aagatactga agggcttaaa     180
gaagttataa atgacagata tgatatgttg aatatttcta gtttacggca agatggaaaa     240
acatttatag attttaaaaa atataatgat aaattaccgt tatatataag taatcccaat     300
tataaggtaa atgtatatgc tgttactaaa gaaaacacta ttattaatcc tagtgagaat     360
ggggatacta gtaccaacgg gatcaagaaa attttaatct tttctaaaaa aggctatgag     420
ataggataa                                                             429

<210> SEQ ID NO 18
<211> LENGTH: 142
<212> TYPE: PRT
<213> ORGANISM: Bacillus anthracis

<400> SEQUENCE: 18

Lys Arg Phe His Tyr Asp Arg Asn Asn Ile Ala Val Gly Ala Asp Glu
  1               5                  10                  15

Ser Val Val Lys Glu Ala His Arg Glu Val Ile Asn Ser Ser Thr Glu
                 20                  25                  30

Gly Leu Leu Leu Asn Ile Asp Lys Asp Ile Arg Lys Ile Leu Ser Gly
             35                  40                  45

Tyr Ile Val Glu Ile Glu Asp Thr Glu Gly Leu Lys Glu Val Ile Asn
         50                  55                  60

Asp Arg Tyr Asp Met Leu Asn Ile Ser Ser Leu Arg Gln Asp Gly Lys
 65                  70                  75                  80

Thr Phe Ile Asp Phe Lys Lys Tyr Asn Asp Lys Leu Pro Leu Tyr Ile
                 85                  90                  95

Ser Asn Pro Asn Tyr Lys Val Asn Val Tyr Ala Val Thr Lys Glu Asn
                100                 105                 110

Thr Ile Ile Asn Pro Ser Glu Asn Gly Asp Thr Ser Thr Asn Gly Ile
            115                 120                 125

Lys Lys Ile Leu Ile Phe Ser Lys Lys Gly Tyr Glu Ile Gly
        130                 135                 140
```

ANTHRAX VACCINE

FIELD OF THE INVENTION

This invention relates to vaccines for bacterial toxins from *Bacillus anthracis*.

INTRODUCTION

Anthrax is a disease cause by the sporulating bacteria *Bacillus anthracis*. Humans working with animal products are at risk from contracting anthrax. Areas such as Iran, Turkey, Iraq, Pakistan, and sub-Saharan Africa are hyperendemic for anthrax, although the organism can be found in most areas of the world. Anthrax manifests disease in three different ways. Inhalation, gastrointestinal, and cutaneous anthrax result from inhaling spores, ingesting spores in contaminated meat, or contacting spores in an open wound, respectively. Untreated inhalation or gastrointestinal anthrax has a case fatality rate of essentially 100 percent while cutaneous anthrax has a case fatality rate of up to 25 percent. Previous research has shown that the protective antigen (PA) produced by *B. anthracis* can protect mice from anthrax. Even though the Anthrax vaccine is FDA licensed, reactogenicity is mild to moderate.

Therefore, there is a need for an efficacious vaccine for anthrax useful for protecting humans.

SUMMARY OF THE INVENTION

The present invention satisfies the need discussed above. The present invention relates to a method and composition for use in inducing an immune response which is protective against infection with anthrax.

In this vaccine strategy, a gene coding for a protein of interest is cloned into a VEE virus vector in place of the VEE virus structural genes; the result is a self-replicating RNA molecule, a replicon, that encodes its own replicase and transcriptase functions, and in addition makes abundant quantities of mRNA encoding the foreign protein. When replicon RNA is transfected into eukaryotic cells along with two helper RNAs that express the VEE structural proteins (glycoproteins and nucleocapsid), the replicon RNA is packaged into VEE virus-like particles by the VEE virus structural proteins, which are provided in trans. Since the helper RNAs lack packaging signals neccessary for further propagation, the resulting VEE replicon particles (VRPs) which are produced are infectious for one cycle but are defective thereafter. Upon infection of an individual cell with a VRP, an abortive infection occurs in which the infected cell produces the protein of interest in abundance, is ultimately killed by the infection, but does not produce any viral progeny (Pushko et al., 1997, *Virology* 239, 389-401).

The PA gene which contains a prokaryotic secretory signal and the entire 83 kDa coding sequence (Welkos et al., 1988, *Gene* 69, 287-300), was inserted into the VEE replicon vaccine vector (FIG. 1) and have demonstrated high level expression of this bacterial protein in eukaryotic cells in culture. Mice, either the C57BL/6 strain or the A/J strain, inoculated with VRP containing the PA-replicon produced high specific antibody titers and were protected from developing anthrax when challenged subcutaneously with *B. anthracis*.

Therefore, it is one object of the present invention to provide a VEE virus replicon vector comprising a VEE virus replicon and DNA fragments encoding the PA protein from *B. anthracis*.

It is another object of the present invention to provide a self replicating RNA comprising the VEE virus replicon and any of the *B. anthracis* fragments described above.

It is another object of the present invention to provide infectious VEE virus replicon particles produced from the VEE virus replicon RNA described above.

It is further an object of the invention to provide an immunological composition for the protection of mammals against *B. anthracis* infection comprising VEE virus replicon particles containing any of the *B. anthracis* fragments described above or a combination of different VEE virus replicons each having a different *B. anthracis* fragment.

BRIEF DESCRIPTION OF THE DRAWINGS

These and other features, aspects, and advantages of the present invention will become better understood with reference to the following description and appended claims, and accompanying drawings where:

Figure 1:
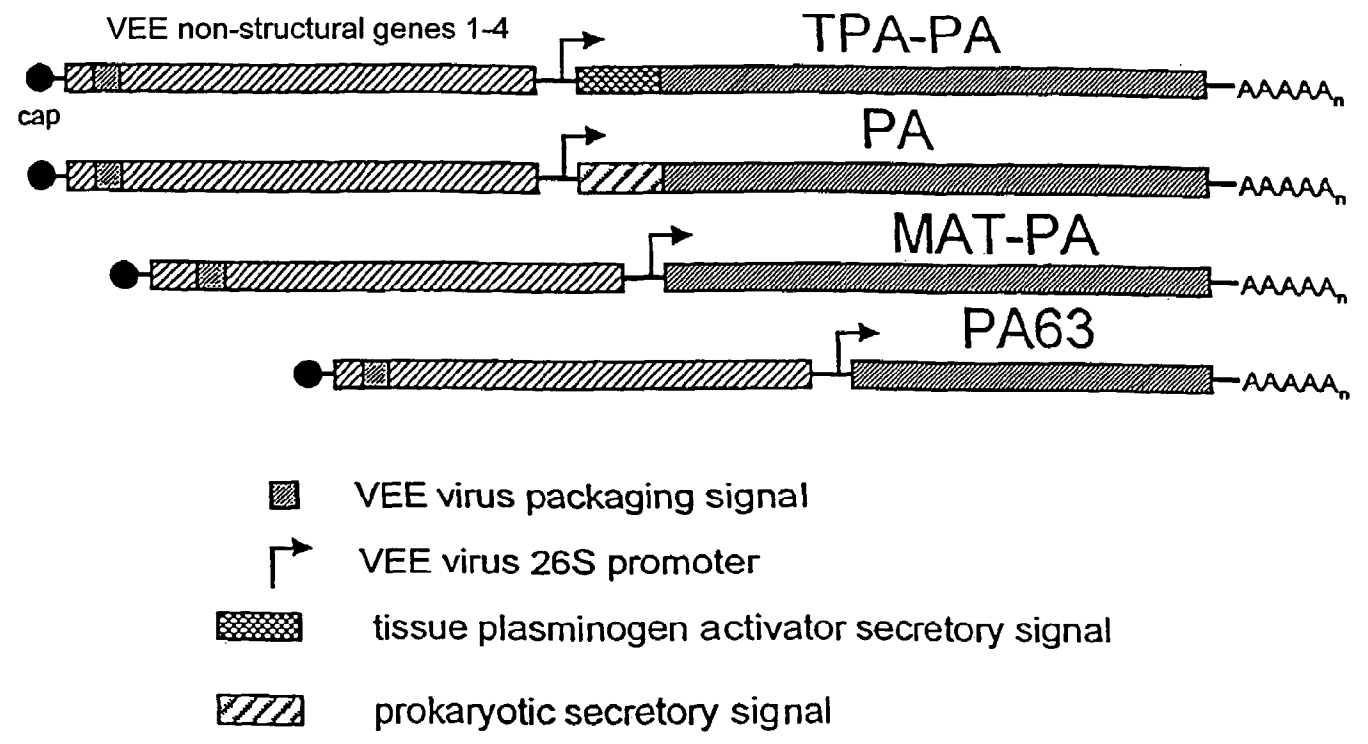

FIG. 1. Diagram of the protective antigen (PA) replicon constructs. The PA replicons are similar to the full-length VEE RNA except that the open reading frame encoding the VEE structural proteins was replaced with the PA genes.

FIGS. 3A and 3B. ELISA titers for mice (A, C57Bl/6 mice; B, A/J mice) immunized with PA-VRP. GMTs only includes those mice that survived challenge. a) Received 0.2 ml on day 0 and 28. b) Received $10^7$ iu on day 0 and 28. c) Received $10^7$ iu PA-VRP on day 0, 28, 56, and 84; C57Bl/6 mice that died, titer=100; A/J mice that died, titer=400. d) Received $10^7$ iu PA-VRP on day 0, 28, and 56; C57Bl/6 mice that died, titers=400, 100, 100; A/J mice that died, titers=102400, 100, 1600. e) Received $10^7$ iu PA-VRP on day 0, and 28; C57Bl/6 mice that died, GMT=1313; A/J mice that died, GMT=1766. Mice were challenged 28 days after last inoculation with 18-32 $LD_{50}$ Sterne strain for C57Bl/6 and 12-25 $LD_{50}$ Sterne strain for A/J mice.

DETAILED DESCRIPTION

Figure 2:
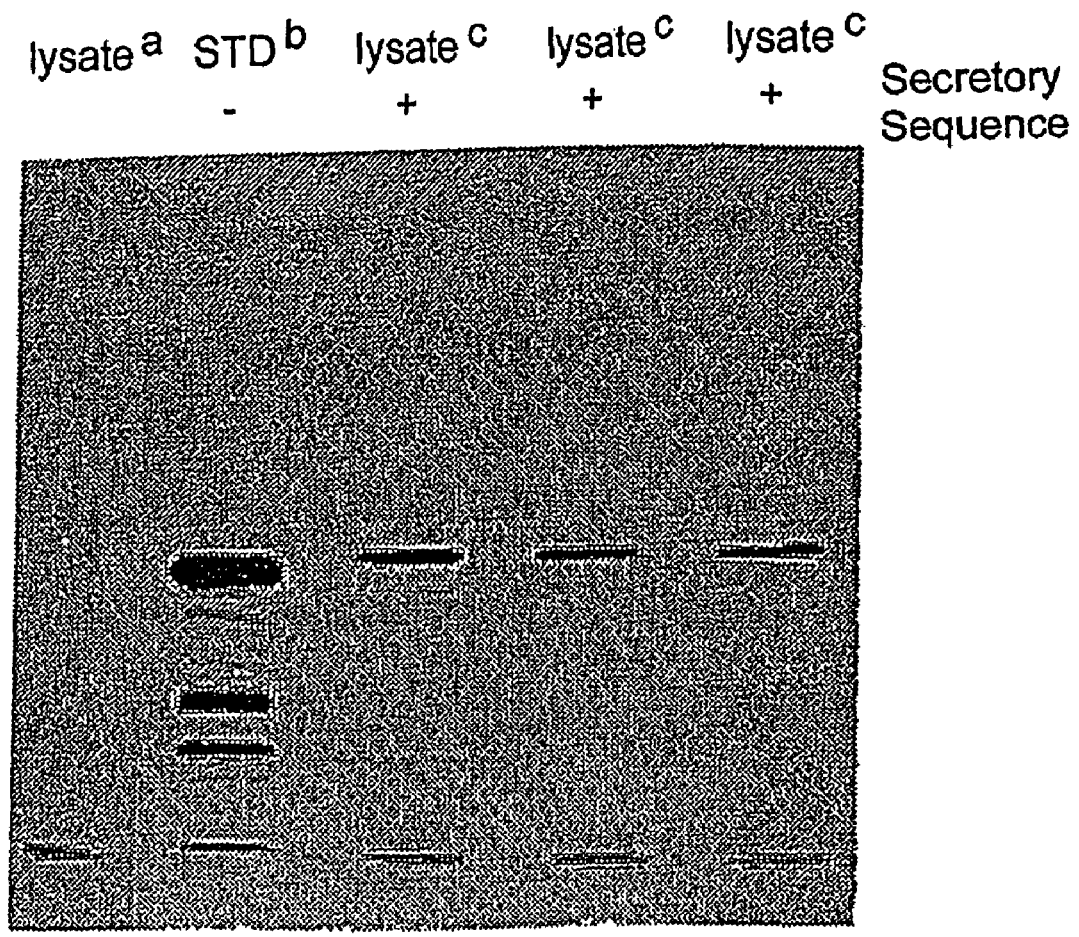
FIG. 2. Western blot of BHK cell lysates showing expression of anthrax protective antigen from recombinant VEE replicons. a) uninfected cell lysate; b) recombinant expression product from *B. anthracis*; c) infected cell lysate.

In the description that follows, a number of terms used in recombinant DNA, virology and immunology are extensively utilized. In order to provide a clearer and consistent understanding of the specification and claims, including the scope to be given such terms, the following definitions are provided.

Replicon. A replicon is equivalent to a full length virus from which all of the viral structural proteins have been deleted. A multiple cloning site can be cloned into the site previously occupied by the structural protein genes. Virtually any heterologous gene may be cloned into this cloning site. Transcription of the RNA from the replicon yields an RNA capable of initiating infection of the cell identically to that seen with the full-length infectious virus clone. However, in lieu of the viral structural proteins, the heterologous antigen is expressed. This system does not yield any progeny virus particles because there are no viral structural proteins available to package the RNA into particles.

Particles which appear structurally identical to virus particles can be produced by supplying structural proteisn for packaging of the replicon RNA in trans. This is typically done with two helpers also called defective helper RNAs. One helper consists of a full length infectious clone from which the nonstructural protein genes and the glycoprotein genes are deleted. The helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNA's are transcribed in vitro and co-transfected with replicon RNA. Because the replicon RNA retains the sequences for packaging by the nucleocapsid protein, and because the helpers lack these sequences, only the replicon RNA is packaged by the viral structural proteins and released from the cell. The particles can then by inoculated into animals similar to parent virus. The replicon particles will initiate only a single round of replication because the helpers are absent, they produce no progeny virus particles, and express only the viral nostructural proteins and the product of the heterologous gene cloned in place to the structural proteins.

The VEE virus replicon is a genetically reorganized version of the VEE virus genome in which the structural proteins genes are replaced with a gene from an immunogen of interest, in this invention, the *B. anthracis* proteins. The result is a self replicating RNA (replicon) that can be packaged into infectious particles using defective helper RNAs that encode the glycoprotein and capsid proteins of the VEE virus.

Subject. Includes both human, animal, e.g., horse, cattle, donkey, monkey, pig, dog, guinea pig, mouse, hamster, avian e.g., chicken, pheasant or turkey, fish and other marine animals, and insects such as mosquito.

In one embodiment, the present invention relates to a recombinant DNA molecule that includes a VEE replicon and a DNA sequence encoding the non-toxic protective antigen (PA) from *B. anthracis*. The sequence for PA has been determined and has been deposited in GenBank at accession no. M22589. The PA sequence encodes a prokaryotic secretory signal in addition to the entire sequence encoding the 83 Kd PA (SEQ ID NO:1). Other nucleic acid sequences related to this invention include sequences wherein the secretory signal has been removed (MAT-PA) (SEQ ID NO:2), or replaced with other secretory signals known to people in the art such as the tissue plasminogen activator (TPA) secretory signal resulting in a DNA fragment encoding TPA-PA (SEQ ID NO:3). Nucleic acid sequences included in this invention are sequences encoding the active form of PA, a 63 kDa protein, termed PA63 (SEQ ID NO:4). In addition, isolated nucleic acid molecules of the invention include DNA molecules which comprise a sequence substantilly differenct from those described above but which, due to the degeneracy of the genetic code, still encode the *B. anthracis* proteins described and specified in SEQ ID NO:5 (TPA-PA), SEQ ID NO:6 (PA), SEQ ID NO:7 (MAT-PA), and SEQ ID NO:8 (PA63). Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

Nucleic acid molecules of the present invention may be in the form of RNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the antisense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The present invention is further directed to nucleic acid molecules encoding portions or fragments of the nucleotide sequences described herein. Fragments include portions of the nucleotide sequences of at least 10 contiguous nucleotides in length selected from any two integers, one of which representing a 5' nucleotide position and a second of which representing a 3' nucleotide position, where the first nucleotide for each nucleotide sequence is position 1. That is, every combination of a 5' and 3' nucleotide position that a fragment at least 10 contiguous nucleotide bases in length or any integer between 10 and the length of an entire nucleotide sequence minus 1.

The present invention further relates to variants of the nucleic acid molecules of the present invention, which encode portions, analogs or derivatives of the *B. anthracis* polypeptides described above. Variants may occur naturally, such as a natural allelic variant. By an "allelic variant" is intended one of several alternate forms of a gene occupying a given locus of a chromosome of an organism. Non-naturally occuring variants may be produced by known mutagenesis techniques. Such variants include those produced by nucleotide substitution, deletion, or addition of one or more nucleotides in the coding or noncoding regions or both. Alterations in the coding regions may produce conservative or nonconservative amino acid substitutions, deletions, or additions. Especially preferred among these are silent substitutions, additions, and deletions which do not alter the properties and activities of the *B. anthracis* polypeptides disclosed herein or portions thereof. Also preferred in this regard are conservative substitutions.

In another embodiment, the present invention relates to a recombinant DNA molecule that includes a vector and a DNA sequence as described above. The vector can take the form of a plasmid, phage, cosmid, YAC, eukaryotic expression vector such as a DNA vector, *Pichia pastoris*, or a virus vector such as for example, baculovirus vectors, retroviral vectors or adenoviral vectors, and others known in the art. The cloned gene may optionally be placed under the control of (i.e., operably linked to) certain control sequences such as promoter sequences, or sequences which may be inducible and/or cell type-specific. Suitable promoters will be known to a person with ordinary skill in the art. The expression construct will further contain sites for transcription initiation, termination and, in the transcribed region, a ribosome binding site for translation. When the DNA sequences described above are in a replicon expression system, such as the VEE replicon described above, the proteins can be expressed in vivo. The DNA sequence for any of the *B. anthracis* proteins described above can be cloned into the multiple cloning site of a replicon such that transcription of the RNA from the replicon yields an infectious RNA containing the *B. anthracis* protein or proteins of interest. Use of helper RNA containing sequences necessary for encapsulation of the viral transcript will result in the production of viral particles containing replicon RNA which are able to infect a host and initiate a single round of replication resulting in the expression of the *B. anthracis* proteins. Such replicon constructs include those listed in Table 1.

TABLE 1

| Replicon Plasmid Name | expresses |
|---|---|
| p3014-TPA-PA | TPA signal, 5 amino acids of C terminal end of prokaryotic secretory signal, and the 83kDa mature protein. |
| p3014-PA | 29 amino acid prokaryotic secretory signal, and the 83kDa mature protein secreted by *B. anthracis* |
| p3014-MAT-PA | 83kDa mature protein |
| p3014-PA63 | 63kDa protein (minus 20kDa N-terminal end that is naturally cleaved off by furin proteases at host cell membrane surface) |
| p3014-sub-domains | subdomain #1: from nucleotide 1891 to 2391; subdomain #2: from nucleotide 2392 to 2658; subdomain #3: from nucleotide 2659 to 3351; subdomain #4: from nucleotide 3352 to 3669; subdomain #5: from nucleotide 3670 to 4098 (Subdomains are numbered according to Welkos et al., 1988, supra, determined on subdomains present in the crystal structure, Petosa, et al., 1997, Nature 385, 833-838). |

The VEE constructs containing anthrax proteins can be used as a DNA vaccine, or for the production of RNA molecules as described below.

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see *Current Protocols in Molecular Biology*. Frederick M. Ausubel et al. (eds.), John Wiley and Sons, Inc. The RNA molecules can be used, for example, as a nucleic acid vaccine, or to transfect cells along with RNA from helper plasmids, one of which expresses VEE glycoproteins and the other VEE capsid proteins, as described above, in order to obtain replicon particles.

Introduction of the construct into the host cell can be effected by calcium phosphate transfection, electroporation, infection, and other methods known in the art and described in standard laboratory manuals such as *Current Protocols in Molecular Biology*, Ausubel, F. M. et al. (Eds), Wiley & Sons, Inc. All documents cited herein supra and infra are hereby incorporated in their entirety by referece thereto.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to rat and human). Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to a sequence encoding an IgG molecule, an adjuvant, a carrier, or an agent for aid in purification of protein of the invention,-such as glutathione S-transferase. The recombinant molecule can be suitable for transfecting eukaryotic cells, for example, mammalian cells and yeast cells in culture systems. *Saccharomyces cerevisiae, Saccharomyces carlsbergensis*, and *Pichia pastoris* are the most commonly used yeast hosts, and are convenient fungal hosts. Control sequences for yeast vectors are known in the art. Mammalian cell lines available as hosts for expression are known in the art and include many immortalized cell lines available from the American Type Culture Collection (ATCC), such as baby hamster kidney (BHK) cells, MRC-5 cells and vero cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences and poly A addition sequences; enhancer sequences which increase expression may also be included, and sequences which cause amplification of the gene may also be desirable. These sequences are known in the art. The transformed or transfected host cells can be used as a source of DNA sequences described above. When the recombinant molecule takes the form of an expression system, the transformed or transfected cells can be used as a source of the protein or polypeptide specified as amino acid sequence in SEQ ID NO:5 (TPA-PA), SEQ ID NO:6 (PA), SEQ ID NO:7 (MAT-PA), and SEQ ID NO:8 (PA63).

A polypeptide or amino acid sequence derived from the amino acid sequences mentioned above, refers to a polypeptide having an amino acid sequence identical to that of a polypeptide encoded in the sequence, or a portion thereof wherein the portion consists of at least 2-5 amino acids, and more preferably at least 8-10 amino acids, and even more preferably at least 11-15 amino acids, or which is immunologically identifiable with a polypeptide encoded in the sequence.

A recombinant or derived polypeptide is not necessarily translated from a designated nucleic acid sequence; it may be generated in any manner, including for example, chemical synthesis, or expression of a recombinant expression system. In addition the polypeptide can be fused to other proteins or polypeptides which increase its antigenicity, such as adjuvants for example.

The recombinant or fusion protein can be used as a vaccine for immunity against anthrax infection or as a diagnostic tool for detection of *bacillus anthracis*. The transformed host cells can be used to analyze the effectiveness of drugs and agents which inhibit anthrax or *B. anthracis* proteins, such as host proteins or chemically derived agents or other proteins which may interact with *B. anthracis* proteins of the present invention to inhibit its function. A method for testing the effectiveness of an anti-anthrax drug or agent can for example be the rat anthrax toxin assay (Ivins et al. 1984, *Infec. Immun.* 52, 454-458 and Ivins et al. 1986) or a skin test in rabbits for assaying antiserum against anthrax toxin (Belton and Henderson, 1956, *Br. J. Exp. Path.* 37, 156-160).

In another embodiment, the present invention relates to an anthrax vaccine comprising one or more replicon particles derived from one or more replicons encoding one or more *B. anthracis* proteins or polypeptides as described above. The present invention relates a method for providing immunity against anthrax said method comprising administering one or more replicon particles containing any combination of the *B. anthracis* proteins to a subject such that a protective immune reaction is generated.

Vaccine formulations of the present invention comprise an immunogenic amount of a replicon particle, resulting from one of the replicon constructs described above, or a combination of replicon particles as a multivalent vaccine, in combination with a pharmaceutically acceptable carrier. An "immunogenic amount" is an amount of the replicon particles sufficient to evoke an immune response in the subject to which the vaccine is administered. An amount of from about $10^2$ to $10^7$ per dose is suitable, more or less can be used depending upon the age and species of the subject being treated. Exemplary pharmaceutically acceptable carriers include, but are not limited to, sterile pyrogen-free water and sterile pyrogen-free physiological saline solution.

Administration of the replicon particles disclosed herein may be carried out by any suitable means, including both parenteral injection (such as intraperitoneal, subcutaneous, or intramuscular injection), by in ovo injection in birds, orally and by topical application of the virus (typically carried in the pharmaceutical formulation) to an airway surface. Topical application of the virus to an airway surface can be carried out by intranasal administration (e.g. by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known; and any conventional technique can be employed. An "immunogenic amount" is an amount of the replicon particles sufficient to evoke an immune response in the subject to which the vaccine is administered.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more constructs or replicating RNA described above can be use in any combination effective to elicit an immunogenic response in a subject. Generally, the nucleic acid vaccine administered may be in an amount of about 1-5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The following MATERIALS AND METHODS were used in the examples that follow.

Plasmids. Construction of the VEE replicon, capsid (C-) helper, and glycoprotein (GP-) helper plasmids was previously described (Pushko, 1997, supra). The PA gene from nucleotide 1804 to 4098 (SEQ ID NO:1) (Welkos et al., 1988, supra) was cloned into the VEE replicon plasmid as a BamHI/BamHI fragment utilizing a shuttle vector. TPA-PA (SEQ ID NO:3), MAT-PA (SEQ ID NO:2), and PA63 (SEQ ID NO:4) were PCR amplified using forward and reverse primers which also contained the ClaI recognition site. The PCR products were agarose gel purified and ligated into the T/A vector pCR2.1 (Invitrogen, Inc.). The PA genes, after digestion of pCR2.1-PA's with ClaI, were ligated into the VEE replicon plasmid. The Lassa nucleocapsid replicon (Lassa N-replicon) was constructed as previously described (Pushko, 1997, supra) and used as a negative control replicon.

Production of VRP. Plasmid templates for the PA-replicons, C-helper, GP-helper, and the Lassa N-replicon were linearized by digestion with NotI at a unique site downstream from the coding sequences, and capped run-off transcripts were prepared in vitro using T7 RNA polymerase. Packaging of the replicons into VEE replicon particles (VRPs) was accomplished by electroporating the replicon RNA and the two helper RNAs into BHK cells. VRPs were harvested between 20 and 27 hours after transfection and purified from cell culture supernatants by ultracentrifugation through a discontinuous sucrose gradient (20%). After reconstituting the pelleted VRP in 1/50 volume phosphate buffered saline, the VRPs were stored at −70° C.

Analysis of expression products and titration of VRP. Subconfluent monolayers were infected with PA-VRP's (either TPA-PA, PA, MAT-PA, or PA63) or Lassa N-VRP (m.o.i.=2) or cell suspensions were electroporated with replicon RNA. Cells were harvested at approximately 20-24 hours and expressed proteins were separated by SDS-PAGE. Visualization of PA proteins was accomplished using a chemiluminescence western blot assay and antibodies specific for each protein. Titration of VRPs was accomplished by infecting subconfluent monolayers with increasing dilutions of purified VRP. Antigen positive cells were visualized in an indirect immunofluorescence assay using a monoclonal antibody specific for each protein, or in a direct immunofluorescence assay using an FITC-conjugated monkey anti-Lassa serum.

Immunization of mice. Mice were inoculated 1 to 4 times at 28 day intervals with $10^5$ to $10^7$ infectious units (iu) of either PA-VRP or Lassa N-VRP (negative control). Positive control mice for the anthrax study were inoculated subcutaneously with 0.2 ml of anthrax vaccine at 28 day intervals. Serum for ELISA was obtained 2 days before each inoculation and 3 days before challenge.

Enzyme-linked immunosorbent assay (ELISA). Microtiter plates were coated with protective antigen (gift from Joe Farchaus, Bacteriology Division) (1 ug/ml) in PBS and allowed to absorb overnight at 4° C. Four fold serum dilutions in blocking buffer were applied to the plates and incubated at 37° C. for 1 hour. After washing, an anti-mouse secondary antibody (HRP conjugated) was added to the plate and incubated for an additional hour at 37° C. After washing, bound antibody was detected colorimetrically using ABTS as a substrate.

Challenge of Mice.

Anthrax challenge: C57BL/6 or A/J mice were challenged subcutaneously with 12-32 $LD_{50}$ B. anthracis (Sterne) 31 days after the last inoculation.

EXAMPLE 1

Packaging and Expression of PA-Replicon

The PA-replicon was efficiently packaged into VRPs using the double helper system. Stock solutions contained about $10^8$ infectious units of purified PA-VRP per milliliter. No replication competent VEE virus was detected in any of the preparations. A western blot of cell lysates, generated from BHK cells infected with PA-VRP, demonstrates a product of approximately 85 kDa (FIG. 2). Because the PA-VRP expression product contains a 29 amino acid prokaryotic secretory signal, which is cleaved from the standard, the PA product from the BHK cells appears larger than the PA standard.

EXAMPLE 2

Protection against challenge with B. anthracis

Figure 3B:
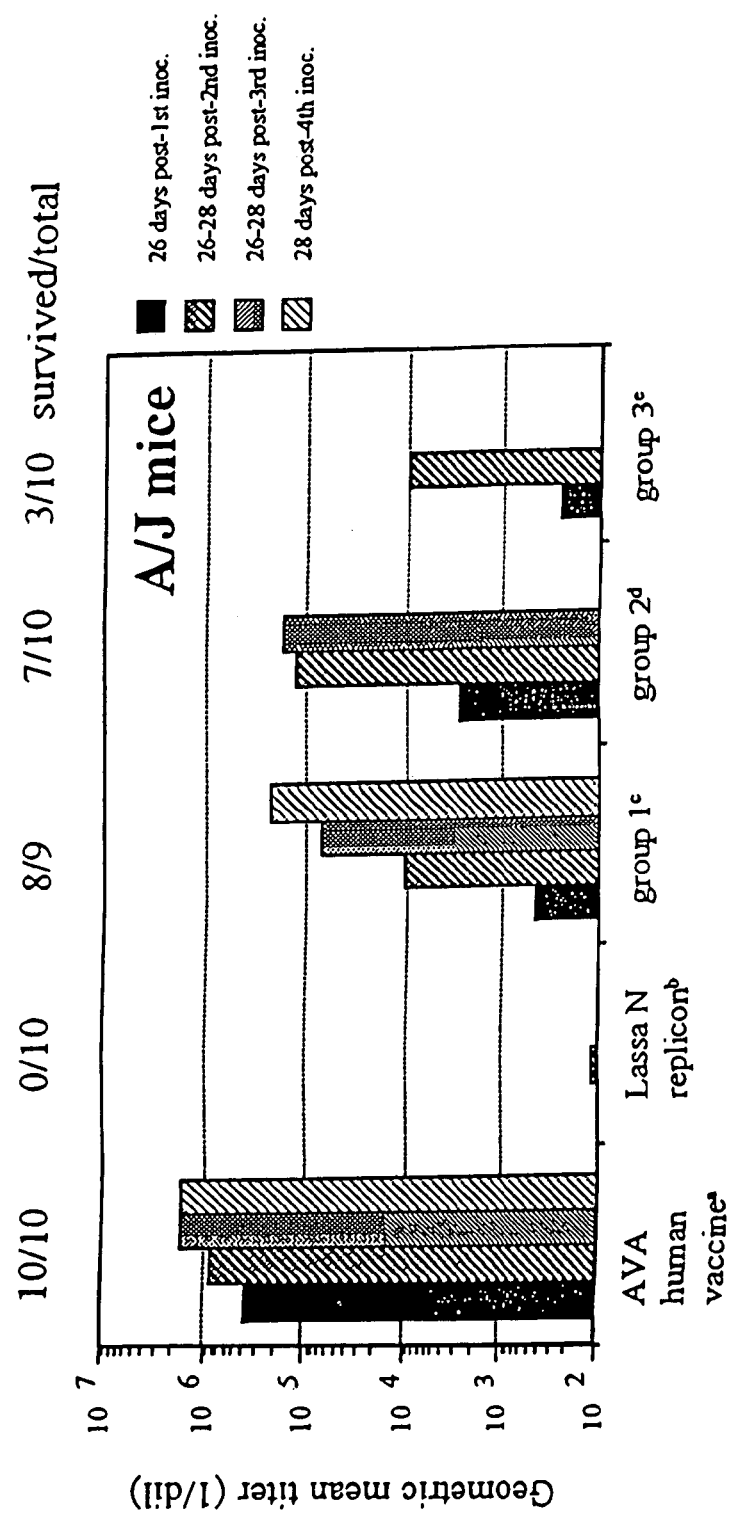
Figure 4:
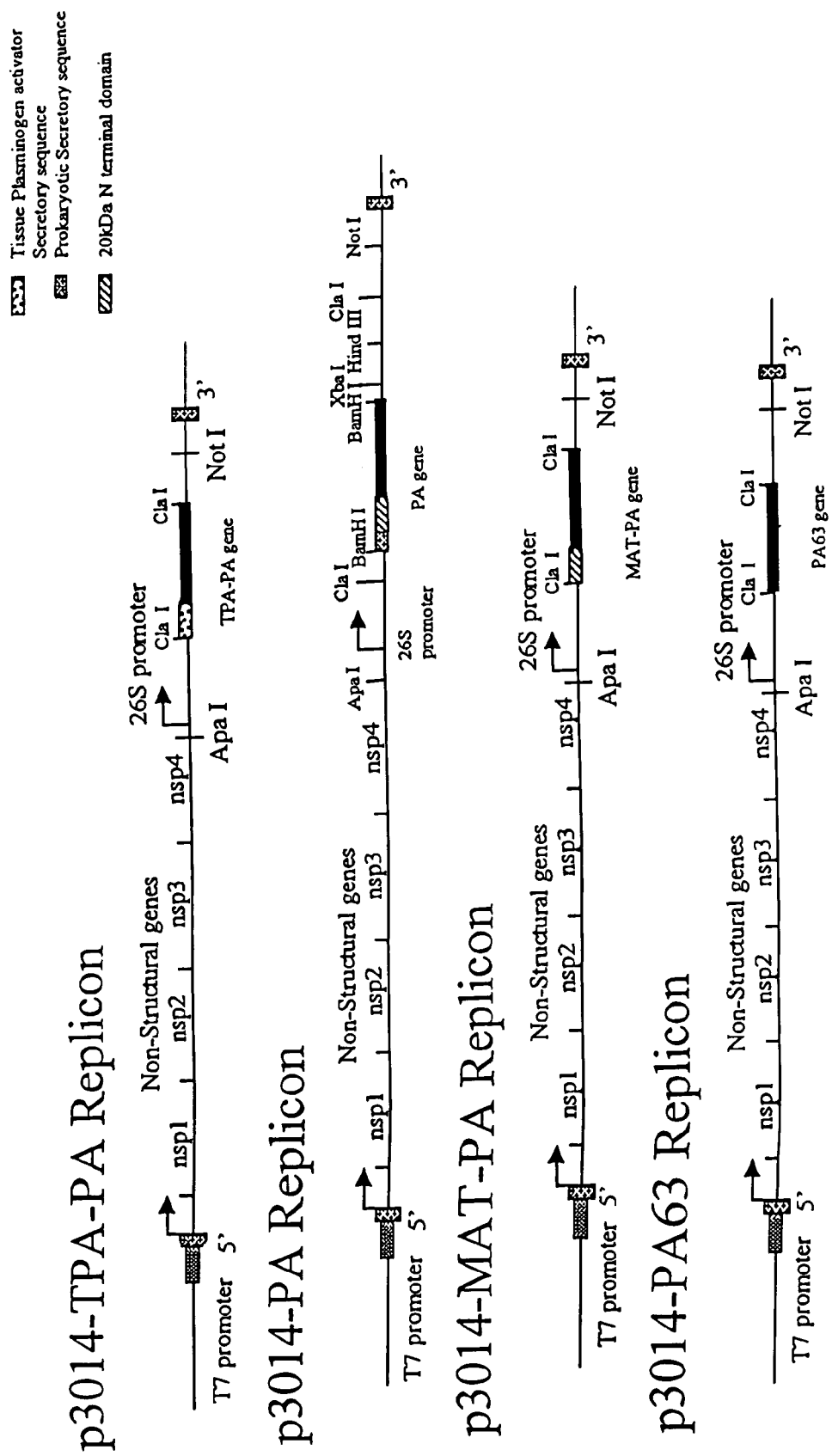
FIG. 4. Schematic representation of constructs containig PA.

The results of the animal studies demonstrated that PA from B. anthracis could be used to immunize and protect mice from a lethal challenge of B. anthracis (Sterne strain). Although the Sterne strain is attenuated in some animals, it is virulent in mice. Controls in the experiment included mice vaccinated with the current human vaccine (anthrax vaccine absorbed, AVA) which protected all mice, and mice immunized with the Lassa N-replicon which expressed an antigen irrelevant to anthrax protection which failed to protect the mice. FIG. 3A shows ELISA titers and survival for C57Bl/6 mice inoculated with two to four doses of PA-VRP. Seventy percent of the C57Bl/6 mice which received three inoculations of the PA-VRP were protected whereas 90% of the C57Bl/6 mice which received four inoculations were protected from an otherwise lethal challenge of B. anthracis (Sterne strain). The geometric mean of the serum ELISA titers to PA of C57Bl/6 mice given four doses of the PA-replicon was 150500, as compared to 264 for mice that were inoculated with the negative control replicon. FIG. 3B shows ELISA titers and survival for A/J mice inoculated with two to four doses of PA-VRP. Three inoculations of the PA-VRP protected 70% of the A/J mice, whereas four inoculations protected 90% of the A/J mice from an otherwise lethal challenge of the B. anthracis (Sterne strain). The geometric mean of the serum ELISA titers against PA in A/J mice given four doses of the PA-replicon was 223336 as compared to 100 for mice which were inoculated with the negative control replicon. As expected, none of the mice (from either strain) which were inoculated with the negative control replicon survived challenge with B. anthracis (Sterne strain).

Discussion/Conclusion

Since VEE virus replicates in the cytoplasm of eukaryotic cells, the VEE replicon vaccine vector is a useful tool for the expression of prokaryotic genes in eukaryotic cells. Cytoplasmic expression of genes alleviates the difficulties imposed by splicing and nuclear transport of mRNA. We used the VEE replicon as a way to express the prokaryotic PA gene in eukaryotic cells and to develop a new vaccine candidate against anthrax.

The human AVA contains mostly PA protein and is presumed to protect humans by eliciting an antibody response that can neutralize the PA portion of anthrax toxin produced by invading B. anthracis. After neutralization of the toxin, the immune system destroys the invading bacteria. In order to model the human disease, we chose to use mice and the Sterne strain of B. anthracis. The Sterne strain produces anthrax toxin (encoded on the pXO1 plasmid) but lacks a capsule (encoded on the pXO2 plasmid). Mice exposed to large quantities of Sterne (ranging from $10^3$ to $10^8$ spores for the different mouse strains) are not able to overcome the effects of the toxin produced by the bacteria so they succumb to infection. We hypothesized that by immunizing the mice with PA, thereby inducing neutralizing antibodies to the PA portion of the toxin produced by a challenge inoculum, that the mice would be protected.

A VEE replicon was constructed which expressed the PA gene from B. anthracis and was evaluated for in vitro expression, in vivo immunogenicity, and protective efficacy. C57Bl/6 and A/J mice demonstrated increasing antibody responses to PA when inoculated with increasing doses of PA-VRP. The two mouse strains inoculated with up to four doses of PA-VRP displayed increased protection against a lethal challenge with B. anthracis (Sterne strain). The use of mice and the Sterne strain of B. anthracis useful as a model system for studying the immunogenicity and efficacy of replicon based anthrax vaccines.

What is claimed is:

1. A recombinant DNA construct consisting of:
   (i) an expression vector,
   (ii) the isolated sequence of nucleotides from position 3670 to position 4098 of the p3014 plasmid (SEQ ID NO:17),
   (iii) a 26S promoter operably linked to the sequence of (ii),
   (iv) a start codon operably linked to the sequence of (ii),
   (v) a stop codon operably linked to the sequence of (ii), and
   (vi) a PolyA signal operably linked to the sequence of (ii).

2. The recombinant DNA construct according to claim 1, wherein the expression vector is prokaryotic vector.

3. The recombinant DNA construct according to claim 1, wherein the expression vector is a eukaryotic vector.

4. The recombinant DNA construct according to claim 1, wherein the expression vector is a Venezuelan Equine Encephalitis (VEE) replicon vector.

5. Isolated or Purified RNA produced from a recombinant DNA construct consisting of:

(i) an expression vector,
(ii) the isolated sequence of nucleotides from position 3670 to position 4098 of the p3014 plasmid (SEQ ID NO:17),
(iii) a 26S promoter operably linked to the sequence of (ii),
(iv) a start codon operably linked to the sequence of (ii),
(v) a stop codon operably linked to the sequence of (ii), and
(vi) a PolyA signal operably linked to the sequence of (ii).

6. Infectious alphavirus particles produced from packaging the self-replicating RNA of claim 5.

7. The infectious alphavirus particles of claim 6, wherein the aiphavirus is VEE.

8. A pharmaceutical composition comprising infectious VEE particles according to claim 7 in an effective immunogenic amount in a pharmaceutically acceptable carrier.

9. A pharmaceutical composition comprising a recombinant DNA construct construct consisting of:

(i) anexpressionvector,
(ii) the isolated sequence of nucleotides from position 3670 to position 4098 of the p3014 plasmid (SEQ ID NO:17),
(iii) a 26S promoter operably linked to the sequence of (ii),
(iv) a start codon operably linked to the sequence of (ii),
(v) a stop codon operably linked to the sequence of (ii), and
(vi) a PolyA signal operably linked to the sequence of (ii) in an effective amount, in a pharmaceutically acceptable carrier.

10. A vaccine for anthrax comprising infectious viral particles containing VEE replicon RNA encoding a *B. anthracis* peptide fragment, wherein the peptide fragment is encoded by the isolated sequence of nucleotides from position 3670 to position 4098 of the p3014 plasmid (SEQ ID NO:17).

* * * * *